United States Patent
Zhang et al.

(10) Patent No.: US 6,772,009 B2
(45) Date of Patent: Aug. 3, 2004

(54) METHOD AND APPARATUS FOR ADJUSTING THE SENSING THRESHOLD OF A CARDIAC RHYTHM MANAGEMENT DEVICE

(75) Inventors: Geng Zhang, Vadnais Heights, MN (US); Qingsheng Zhu, Little Canada, MN (US); Laura Mepham, Shoreview, MN (US); Jesse W. Hartley, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 261 days.

(21) Appl. No.: 10/152,211

(22) Filed: May 20, 2002

(65) Prior Publication Data

US 2002/0165587 A1 Nov. 7, 2002

Related U.S. Application Data

(62) Division of application No. 09/410,403, filed on Oct. 1, 1999, now Pat. No. 6,418,343.

(51) Int. Cl.[7] .............................................. A61N 1/365
(52) U.S. Cl. ........................................... 607/9; 607/28
(58) Field of Search ................................ 600/509, 521; 607/9, 28; 128/901, 902

(56) References Cited

U.S. PATENT DOCUMENTS

| | | | |
|---|---|---|---|
| 3,927,677 A | 12/1975 | Gobeli et al. | 128/419 PG |
| 4,708,144 A | 11/1987 | Hamilton et al. | 128/419 PG |
| 4,779,617 A | 10/1988 | Whigham | 128/419 P |
| 4,880,004 A | 11/1989 | Baker, Jr. et al. | 128/419 PG |
| 4,903,699 A | 2/1990 | Baker, Jr. et al. | 128/419 PG |
| 5,117,824 A | 6/1992 | Keimel et al. | 128/419 D |
| 5,269,300 A | 12/1993 | Kelly et al. | 607/4 |
| 5,339,820 A | 8/1994 | Henry et al. | 128/696 |
| 5,365,932 A | 11/1994 | Greenhut | 128/696 |
| 5,374,282 A | 12/1994 | Nichols et al. | 607/18 |
| 5,564,430 A | 10/1996 | Jacobson et al. | 128/697 |
| 5,658,317 A | 8/1997 | Haefner et al. | 607/5 |
| 5,683,431 A | 11/1997 | Wang | 607/28 |
| 5,713,934 A | 2/1998 | Leckrone | 607/28 |
| 5,755,738 A | 5/1998 | Kim et al. | 607/9 |
| 5,913,880 A | 6/1999 | Vonk | 607/27 |
| 5,957,857 A | 9/1999 | Hartley | 600/521 |

FOREIGN PATENT DOCUMENTS

EP 0581010 7/1992 ............ A61N/1/39

OTHER PUBLICATIONS

Wilson, J..H. ,et al. ,"Clinical Evaluation of an Automatic Sensitivity Adjustment Feature in a Dual Chamber Pacemaker", *PACE*, *13* (*10*), (Oct. 1990),pp. 1220–1223.

Primary Examiner—Jeffrey R. Jastrzab
(74) Attorney, Agent, or Firm—Schwegman, Lundberg, Woessner & Kluth, P.A.

(57) ABSTRACT

A method and apparatus for automatically adjusting the sensing threshold of cardiac rhythm management devices. The invention is particularly suited for implementation in devices such as implantable cardiac pacemakers and implantable cardioverter/defibrillators. A method and apparatus are provided in which a noise level and signal level for a sensing channel are determined for each cardiac cycle with the sensing threshold of the channel being adjusted in accordance therewith.

20 Claims, 7 Drawing Sheets

METHOD AND APPARATUS FOR ADJUSTING THE SENSING THRESHOLD OF A CARDIAC RHYTHM MANAGEMENT DEVICE

CROSS-REFERENCE TO RELATED APPLICATION(S)

This application is a division of U.S. patent application Ser. No. 09/410,403, filed on Oct. 1, 1999, now U.S. Pat. No. 6,418,343, the specification of which is incorporated by reference herein.

FIELD OF THE INVENTION

This invention relates generally to a cardiac rhythm management device such as implantable cardiac pacemakers and implantable cardiac defibrillators. In particular the invention pertains to methods and apparatus for automatically adjusting the sensing threshold of such devices.

BACKGROUND

Currently available implantable cardiac rhythm management devices, including bradycardia and tachycardia pacemakers and cardiac defibrillators, have sense amplifier circuits for amplifying and filtering electrogram signals picked up by electrodes placed in or on the heart and which are coupled by suitable leads to the implantable cardiac rhythm management device. In most devices, the signals emanating from the sense amplifier are applied to one input of a comparator circuit whose other input is connected to a source of reference potential. Only when an electrogram signal from the sense amplifier exceeds the reference potential threshold will it be treated as a detected cardiac depolarization event such as an r-wave or a p-wave. The source reference potential may thus be referred to as a sensing threshold.

In the case of a programmable cardiac rhythm management device the prescribing physician can change the threshold potential of the comparator, but in spite of the flexibility which the programmable threshold offers, malsensing of cardiac depolarization will still occur frequently enough to result in patient discomfort and/or deleterious health effects. This may be due to the fact that cardiac depolarization events (intrinsic beats) can result in widely different peak amplitudes, depending on patient activity body position, drugs being used, etc. Lead movement and noise may further impede the detection of cardiac depolarization events. Noise sources may include environmental noise, such as 60 Hz power line noise, myopotentials from skeletal muscle, motion artifacts, baseline wander and T-waves. When the peak amplitudes associated with cardiac depolarization events become too small relative to a programmed threshold, or when noise levels in the electrocardiogram approach the sensing threshold, the likelihood of oversensing increases (i.e., false detection of depolarization events). If the sensing threshold is increased too high in an attempt to overcome the effects of noise, on the other hand, the likelihood of undersensing (i.e., failing to detect depolarization events) is increased. There is a need, therefore, for methods and apparatus that automatically adjust the sensing thresholds of cardiac rhythm management devices on a continuous beat-to-beat basis in a manner that better avoids both undersensing and oversensing.

SUMMARY OF THE INVENTION

The present invention provides a method and apparatus for automatically adjusting the sensing threshold of a cardiac rhythm management device. Such a device may employ both atrial and ventricular sensing channels for sensing atrial and ventricular electrogram signals, where a sensing channel includes a sensing amplifier having one of its inputs connected by a lead to an electrode placed in proximity to either an atrium or a ventricle. The output signal of the sensing amplifier is digitized and passed to a threshold detector that determines whether the amplitude of the signal exceeds a sensing threshold, signifying the detection of either an atrial depolarization event (a p-wave) or a ventricular depolarization event (an r-wave). The device may also include a pulse generator and, associated control circuitry for delivering pacing pulses to the atrium and/or ventricle in response to elapsed time intervals and detected r-waves and p-waves.

In accordance with the invention, atrial and/or ventricular sensing thresholds are automatically adjusted in a manner that attempts to prevent noise signals from being misinterpreted as cardiac depolarization events while at the same time avoiding undersensing of depolarization events that actually occur. In one embodiment, the automatic adjustment is performed by calculating the sensing threshold of a sensing channel based upon a measured amplitude of the depolarization event (i.e., an r-wave or a p-wave) during the current cardiac cycle and a measured current noise level in the channel. A cardiac cycle is defined as the interval between the beginning of one heartbeat and the beginning of another, where the beginning of a heartbeat as defined herein is atrial systole, marked by detection of a p-wave or delivery of an atrial pace, or ventricular systole in the case of a premature ventricular contraction or PVC. The adjustment is preferably performed during the refractory period after either detection of an r-wave or delivery of a ventricular pacing pulse by the device.

In a preferred embodiment, the noise level for a sensing channel is measured during a post-ventricular refractory period. As is conventional, both atrial and ventricular sensing channels are rendered refractory (i.e., where the device ignores detected depolarization events) for a period of time immediately beginning after an r-wave or a ventricular pace. Such a refractory period is referred to as the ventricular refractory period (VRP) for the ventricular channel and the post-ventricular atrial refractory period (PVARP) for the atrial channel. The noise level for a particular channel is measured during a noise measurement window that occurs during the refractory period of the channel, with the sensing threshold being decreased during the noise measurement window for the ventricular channel in order to sense lower amplitude noise activity. The amplitudes of electrogram signals that exceed the decreased sensing threshold during the noise measurement window are measured, and a current noise level is computed based upon the measured amplitudes. The computed current noise level may correspond to, for example, the maximum measured amplitude during the measurement window, an average measured amplitude, or a formula that takes into account the maximum measured amplitude and the noise level calculated for a previous cardiac cycle.

In accordance with the invention, the amplitude of a depolarization event (i.e., a detected r-wave or a p-wave) is measured for the current cardiac cycle and then used along with the current noise level to adjust the sensing threshold for a sensing channel. Preferably, the sensing threshold for a sensing channel is adjusted based upon a current average depolarization event amplitude computed from a combination of a previous average depolarization event amplitude computed for a previous cardiac cycle and, if a depolarization event is detected in the sensing channel for the current cardiac cycle, the current measured amplitude of the depolarization event.

If no depolarization event has been detected in a sensing channel during the current cardiac cycle, it may be surmised that either no such event actually occurred, or that an event occurred but was undersensed. Because of the latter possibility, it would be desirable to adjust the sensing threshold downward (i.e., decrease the threshold) for a sensing channel after a cardiac cycle in which no depolarization event was detected. In accordance with the present invention, therefore, if a heart chamber is paced during a particular cardiac cycle (i.e., because no intrinsic depolarization event was detected), the sensing threshold for that chamber's sensing channel is adjusted in a manner that decreases the threshold. In certain implementations, the sensing threshold is adjusted so that it is decreased unless the noise level has increased from the previous cardiac cycle to such an extent that the same or a higher sensing threshold is warranted. In a preferred embodiment, this is accomplished by performing the adjustment of the sensing threshold for the channel using an average depolarization event amplitude computed for a previous cardiac cycle that is decreased by a specified constant amount.

As aforesaid, when no depolarization event is detected for a particular sensing channel during a cardiac cycle, the sensing threshold for the channel is adjusted using a decreased average depolarization event amplitude, the effect of which is thus to decrease the threshold as long as the noise level is unchanged from the previous cardiac cycle. In the case where no r-wave is detected and the cardiac rhythm management device is operating in a demand ventricular pacing mode, a ventricular pacing pulse is delivered during the current cardiac cycle. In accordance with the invention, delivery of a ventricular pacing pulse during a cardiac cycle causes the ventricular sensing threshold to be adjusted as described above in a manner that tends to decrease the threshold. In the case where no p-wave is detected during a cardiac cycle and the device is operating in a demand atrial pacing mode, however, there are two possibilities: either an atrial pacing pulse was delivered in response to the non-detection of a p-wave, or an r-wave has been detected that is preceded by neither an atrial pacing pulse nor detection of a p-wave. The latter situation indicates either the occurrence of a premature ventricular contraction or undersensing of a p-wave. In accordance with the invention, non-detection of a p-wave causes the atrial sensing threshold to be adjusted as described above in a manner that tends to decrease the threshold whether the non-detection of the p-wave is due to delivery of an atrial pace or due to a premature ventricular contraction occurring during the current cardiac cycle. In other embodiments, the amount by which the atrial sensing threshold is decreased may be different depending on whether an atrial pace or a premature ventricular contraction occurred during a cardiac cycle by, for example, using separate specified constant amounts by which the average p-wave amplitude computed for a previous cycle is decreased.

BRIEF DESCRIPTION OF THE DRAWINGS

In the accompanying drawings described below, like numerals in different figures refer to corresponding elements.

DETAILED DESCRIPTION OF THE INVENTION

The present invention provides an improved method and apparatus for automatically adjusting the sensing threshold of a cardiac rhythm management device capable of sensing intrinsic events of a patient's heart. Such devices in which the invention may find application include implantable cardiac pacemakers and implantable cardioverter/defibrillators. In accordance with the invention, the sensing threshold is automatically adjusted as a function of intrinsic beat amplitude and noise "measured" during a predetermined period immediately following the intrinsic beat detection. The automatic adjustment of the sensing threshold may be implemented for both atrial and ventricular sensing channels and is referred to herein as "autosense." The "measurement" of noise may vary depending upon the mode of autosense for example, atrial autosense or ventricular autosense. The embodiments detailed herein are intended to be taken as representative or exemplary of those in which the improvements of the invention may be incorporated and are not intended to be limiting.

Figure 1:
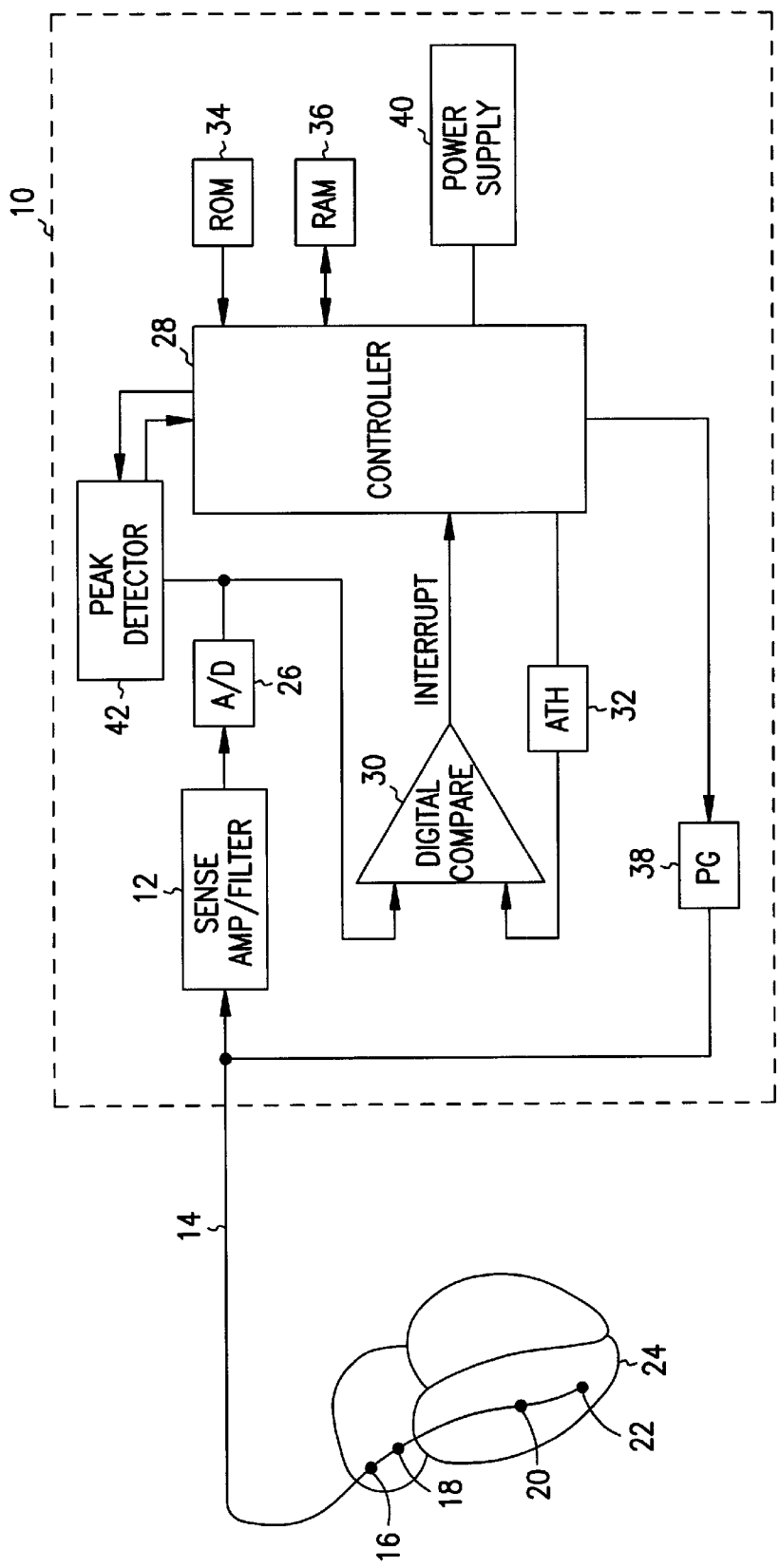
FIG. 1 is a general block diagram of a cardiac rhythm management device which may incorporate the autosense feature of the present invention.

Referring first to FIG. 1, there is illustrated by means of a block diagram, a hardware platform in which the autosense algorithm of the present invention may be utilized. Shown enclosed by the broken line box 10 is circuitry which may be included within a cardiac rhythm management device, such as a bradycardia pacemaker. It is seen to include a sense amplifier/filter 12 having its input connected by a pacing lead 14. The pacing lead 14 is shown having a plurality of electrodes 16–22 coupled to lead 14 and disposed or in the heart 24. An electrogram signal is transmitted through the pacing lead 14 to the sense amplifier 12.

In FIG. 1, the lead 14 is shown as a bipolar single pass VDD or DDD lead, various forms of which are known to those skilled in the art. In this embodiment, the electrodes 20 and 22 are designed to detect ventricular depolarization, while electrodes 16 and 18 sense atrial depolarization. The controller 28 is coupled to power supply 40 and provides a control output to a pulse generator 38 at appropriate times. The resulting pulses are applied over the lead 14 to the electrodes 16, 18, 20 and 22 for providing electrical stimulation to the heart 24. The arrangement shown in FIG. 1 can be used for sensing both intrinsic P-waves and R-waves as well as applying pacing pulses in the atrium and/or ventricle.

The sense amp/filter circuit 12 conditions the electrogram signal and then applies the conditioned signal to an analog-to-digital converter 26 which converts the conditioned sensed signal to corresponding digital values compatible with a peak detector 42. From the analog-to-digital converter 26, the signal is transmitted to both peak detector 42 and a comparator 30. In certain embodiments, the peak detector may include a digital comparator and register, wherein the signal transmitted from the A/D converter 26 is continuously compared with an initial value stored in the peak detector register. If the current signal is greater than the value stored in the peak detector, the current value is loaded into the register value and is then stored in the peak detector register. The peak detector 42 includes a clearing mechanism controlled by the controller 28. Timers to activate and deactivate the peak detector, either external or internal to the controller 28, may also be included. Once the peak detector 42 times out, the final peak detector register value is transmitted to the controller 28. As aforesaid, the signal transmitted from the A/D converter 26 is also applied to an input of the comparator 30, with the reference input of the comparator coming from the contents of register ATH. An interrupt is generated to the controller 28 by the comparator 30 when the signal from the A/D converter 26 exceeds the digital value stored in register ATH, allowing the controller 28 to read the corresponding value stored in peak detector 42 and obtain the maximum value of the sensed signal. The contents of register ATH may thus provide a sensing threshold so that sensed signal having amplitudes below the threshold can be ignored. The contents of register ATH may be updated by the controller 28 in accordance with programmed algorithms to be described below.

The drawing of FIG. 1 shows only one hardware configuration in which the autosense algorithm of the present invention can be implemented. Those skilled in the art can appreciate that the circuit of FIG. 1 can be modified so that, for example, the digital comparator 30 and ATH register 32 can be internal to the controller 28. It is also possible to add an additional digital comparator in parallel with the digital comparator 30 and provide a separate threshold register for corresponding sensing threshold (ST) rather than time sharing the digital comparator 30 between the detection of cardiac depolarization and noise. The controller 28 may be in any of several forms including a dedicated state device or a microprocessor with code, and may include ROM memory 34 for storing programs to be executed by the controller 28 and RAM memory 36 for storing data.

The operation of the autosense algorithm of the present invention is based upon the detection and measurement of noise during a period following a cardiac depolarization or pacing event. (As used herein, the term "depolarization" refers to a detected intrinsic depolarization and not to depolarization produced by a pacing pulse. Although pacing pulses produce cardiac depolarizations, these depolarizations are not usually detected by cardiac rhythm management devices because the sensing amplifiers are "blanked" and the sensing channel rendered refractory for a predetermined period following a pace.) The method of measuring noise may be modified depending upon the hardware constraints of the rhythm management device and whether the device is operating in atrial autosense or ventricular autosense. Atrial autosense refers to the automatic adjustment of the atrial sensing threshold, while ventricular autosense refers to the automatic adjustment of the ventricular sensing threshold. As will be described in greater detail below, ventricular autosensing is performed following a ventricular depolarization or ventricular pace and during a predetermined portion of a subsequent refractory period (i.e., the VRP). During the autosense operation, the sensing threshold is reduced, and the amplitude of each noise deflection is determined. The atrial autosense operation is also performed following a cardiac depolarization and during a predetermined period (which may coincide with the PVARP), the noise amplitude may be determined. Because the atrial refractory period extends from an atrial depolarization or atrial pace through the AV interval and then beyond the ventricular depolarization or pace (i.e., the PVARP), both ventricular and atrial autosensing may be performed during the atrial and ventricular refractory periods that occur during each cardiac cycle. A cardiac cycle is defined as the interval between the beginning of one heartbeat and the beginning of another, where the beginning of a heartbeat is atrial systole, marked by detection of a p-wave or delivery of an atrial pace, or ventricular systole in the case of a premature ventricular contraction or PVC.

The current noise level may be determined as a function of the measured noise amplitude during the predetermined periods described above, e.g., as the maximum measured amplitude. In an alternate embodiment, the noise level is estimated and the number of deflections exceeding the sensing threshold is determined over a predetermined period following a cardiac depolarization. From the current noise level, the sensing threshold may be automatically adjusted by the controller 28, and updating of sensing threshold may be done on a beat-by-beat basis.

Figure 2:
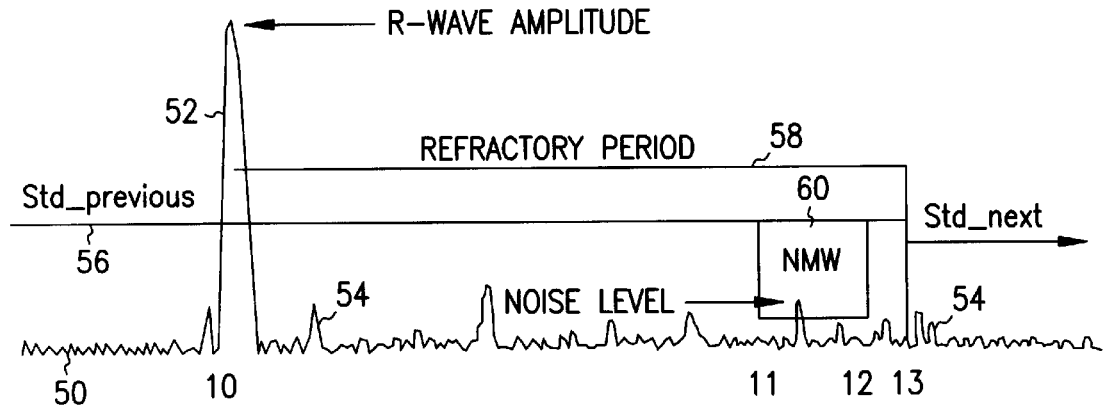
FIG. 2 is a graph of an electrogram showing the noise measurement window implemented for ventricular autosense.

Referring to FIG. 2, there is shown an electrogram signal as it relates to an implantable cardiac rhythm management device operating in a ventricular autosense mode and incorporating the improvements of the present invention. The electrogram signal represented by the waveform 50 includes a cardiac depolarization or r-wave deflection 52 and numerous noise deflections 54. The device is shown as including a sensing threshold which is represented by line 56 and a refractory period represented by line 58. The sensing threshold 56 may be implemented to effectively block out sensing by the controller 28 of all deflections in the waveform 50 that do not have an amplitude value greater than the preset sensing threshold value. As previously mentioned, a comparator may be utilized to provide the sensing threshold, which value may be set to, for example, 0.25 mV.

During ventricular autosense, once a cardiac depolarization is detected at t0, a refractory period is initiated and the sensing threshold 56 is reduced for a period of time (t2–t1), shown as the noise measurement window (NMW) 60 during the refractory period 58, such that the maximum amplitude of noise may be detected and measured. In the preferred embodiment, the NMW ends at least 10 ms prior to the end of the refractory period (t3–t2), thereby reducing the likelihood that a premature ventricular contraction (PVC) will be confused as noise.

Figure 3:
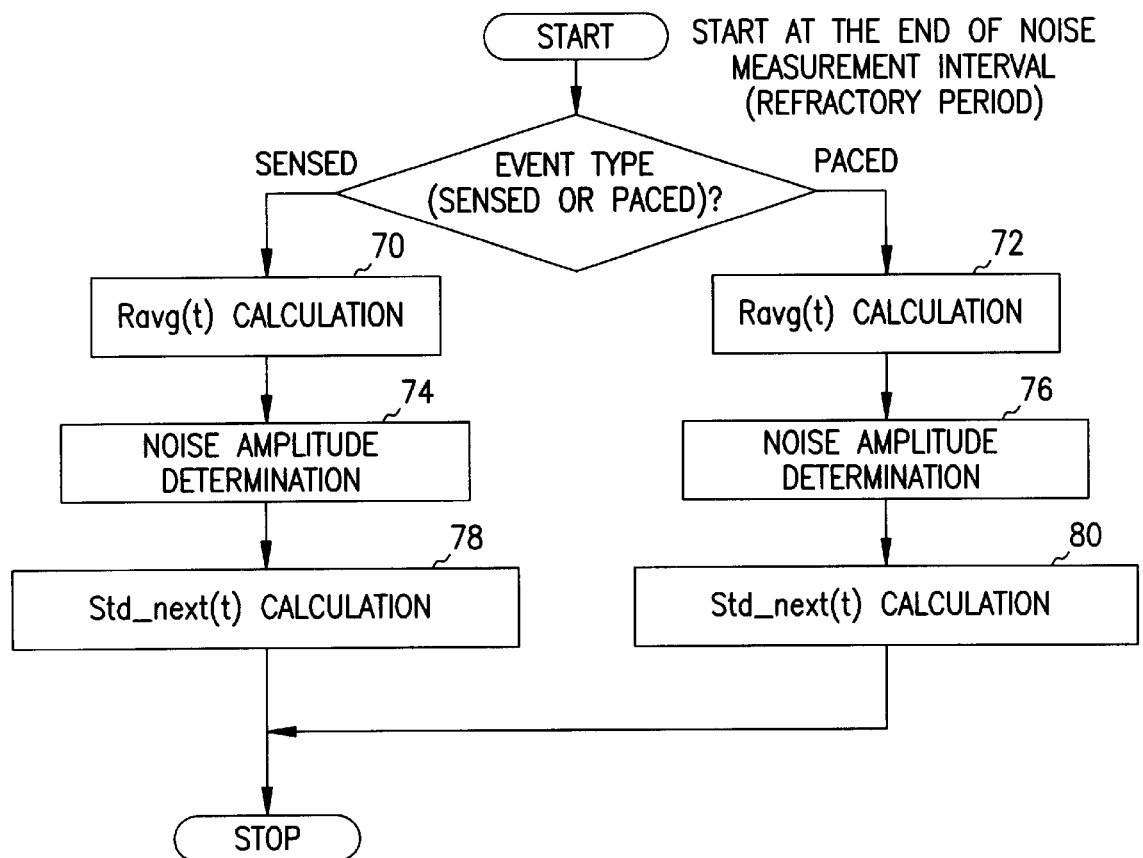
FIG. 3 is a software flow diagram of the autosense algorithm of the present invention following the measurement of noise for ventricular autosense.

Embodied in the controller 28 is a timer and deflection counter capable of measuring the number of deflections having an amplitude that exceeds the sensing threshold during each predetermined period. When the timer times out for each refractory period, the sensing threshold 56 value is adjusted by the controller 28 as a function of the measured noise and intrinsic beat. FIG. 3 shows an algorithm in flowchart form that may be implemented by the controller 28 to adjust the sensing threshold as a function of noise and intrinsic beat during ventricular autosense. This algorithm is executed by a dedicated portion of controller 28 shown in FIG. 1.

Without any limitation intended, when an electrocardiogram excursion picked up on lead 14 is signal processed by the sense amplifier/filter circuit 12 and converted to a digital quantity by A/D converter 26, a digital quantity proportional to the excursion is applied to one input of the digital comparator 30 and to the controller 28. If the electrocardiogram excursion exceeds the ventricular sensing threshold, the controller processes the signal as a cardiac depolarization, measuring the amplitude of the depolarization wave, initiating the refractory period 58 and predetermined period, and measuring the amplitude of noise deflections detected in the noise measurement window 60. Once the refractory period 58 times out, the controller 28 initiates a sequence to determine and adjust the sensing threshold 56. The sequence that the controller 28 follows will now be discussed. First, the detected ventricular depolarization or r-wave amplitude is "smoothed" or "averaged" according to the following equations:

$$Ravg(t)=R(t)/4+((3)Ravg(t-1))/4$$

$$Ravg(t)=Ravg(t-1)-rm,$$

wherein the first equation is applied if the detected ventricular depolarization during the current cycle is intrinsic (See FIG. 3, block 70), and the second equation is applied if no ventricular depolarization was detected during the current cardiac cycle resulting in delivery of a pacing stimulus (see FIG. 3, block 72). R(t) is the current amplitude of the ventricular depolarization, Ravg(t−1) is the previous "smoothed" r-wave amplitude, and rm is a preselected constant that without limitation, may range between 0.001–2.5 mV. The preselected constant, rm, will vary depending upon whether sensing in the atrial autosense or ventricular autosense mode, with 0.14 mV being preferred for ventricular autosense and 0.03 mV being preferred for atrial autosense. Those skilled in the art will recognize and appreciate that the rm may, for convenience be set equal to the resolution of the A/D converter 26 or a multiple thereof. Once a current "smoothed" r-wave amplitude is determined, then the noise level is determined (see blocks 74 and 76) from the following equation:

$$N(t)=\text{Max}[\text{Min}(5\ mV; NWAmp); 0.375\ mV; N(t-1)-rm]$$

wherein NWAmp is the maximum amplitude of noise measured in the noise measurement window 60, N(t−1) is the previously determined noise level, and rm is a preselected constant as described previously. After the noise level and current "smoothed" r-wave amplitude are determined, then a value for the sensing threshold may be determined according to the following equation:

$$Stdnext(t)=\text{Max}[(Ravg(t)-N(t))/x+N(t); ymV; zN(t)]$$

wherein Stdnext(t) is defined as the next ventricular sensing threshold, x is a constant ranging between 1–5 with 2 being preferred for atrial autosense and 3 being preferred for ventricular autosense. In the alternative, x may be set as a function of noise. For example, the following equation may apply:

$$x=Ravg(t)/N(t)$$

Likewise, x may be set equal to the current smoothed ventricular depolarization amplitude (x=Ravg(t)), y is a constant ranging between 0.05–5 mV with 0.10 mV being preferred for intrinsic atrial autosense, 0.75 mV being preferred for intrinsic ventricular autosense, 1.5 m being preferred for paced ventricular autosense, and 0.75 mV being preferred for paced atrial autosense; and z is a constant ranging between 1.0–5.0 with 1.5 being preferred in either atrial or ventricular autosense. In this manner, the sensing threshold will be minimized without reducing the threshold below an acceptable signal to noise (SNR) ratio, thereby improving the rhythm management device's sensing performance and efficiency.

Figure 4:
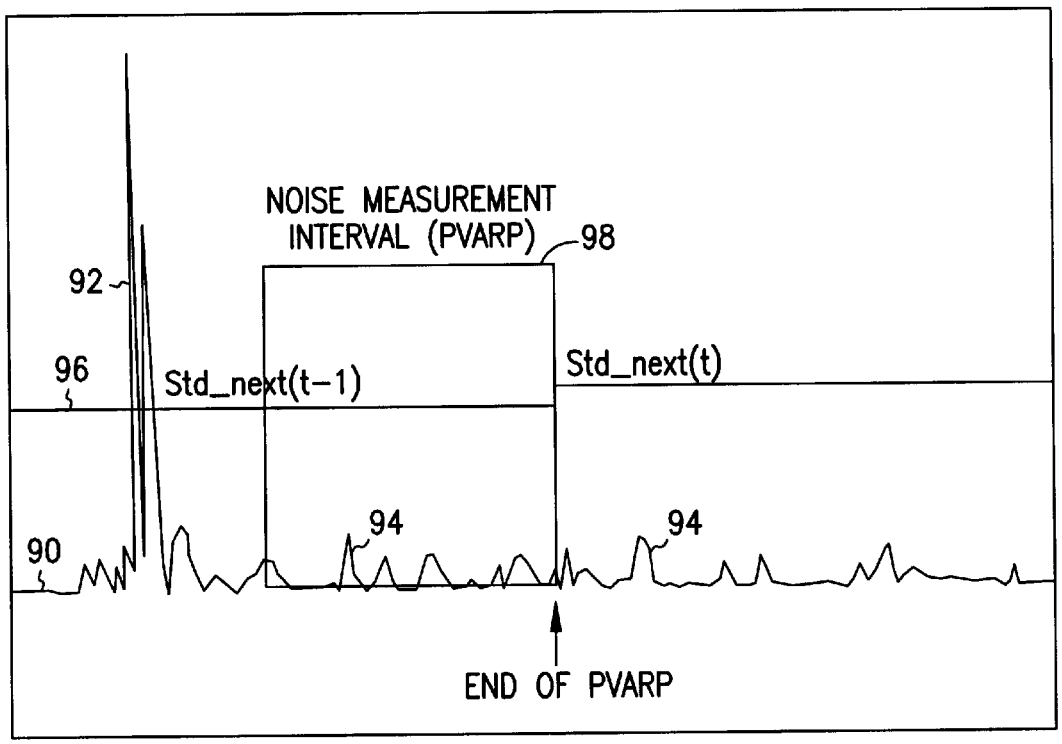
FIG. 4 is a graph of an electrogram showing the noise measurement interval implemented for atria autosense.

Referring next to FIG. 4, there is shown generally an electrocardiogram signal typically received by an implantable cardiac rhythm management device set in an atrial autosense mode that incorporates the improvements of the present invention. The electrogram signal represented by the waveform 90 includes an atrial depolarization or p-wave deflection 92 and numerous noise deflections 94. The operation of the device includes an atrial sensing threshold which is represented by line 96 and a post-ventricular atrial refractory period or PVARP represented by line 98. Although the predetermined period or noise measurement window NMW is shown coinciding with the PVARP interval, those skilled in the art will appreciate that the predetermined period may be initiated prior to or after the PVARP is initiated and may be longer or shorter than the PVARP. Once a p-wave is detected by the controller 28 a timer and counter are initialized. A PVARP is started upon detection of a ventricular depolarization or r-wave. During PVARP, all detected atrial channel deflections are presumed noise, and the maximum amplitude of the noise deflections is determined by the peak detector 42. A conventional RC charging circuit with a long discharging rate may also be utilized such that at the end of PVARP, the RC charging circuit should be discharged completely. Also, the number of detected deflections during the noise measurement interval are counted and the controller 28 ensures that the detected deflections are not resulting from fibrillation or atrial flutter. If the number of detected deflections exceeds a predetermined number, the deflections are presumed noise and the amplitude of the deflections are measured, wherein the predetermined number will correspond to a rate between 300–600 deflections/minute with 400 deflections/minute being preferred. If the number of deflections is less than the predetermined amount but greater than the Upper Rate Limit (URL—a preprogrammed maximum time that the pacer is allowed the pace) are a presumed result of result of or fibrillation.

Figure 5:
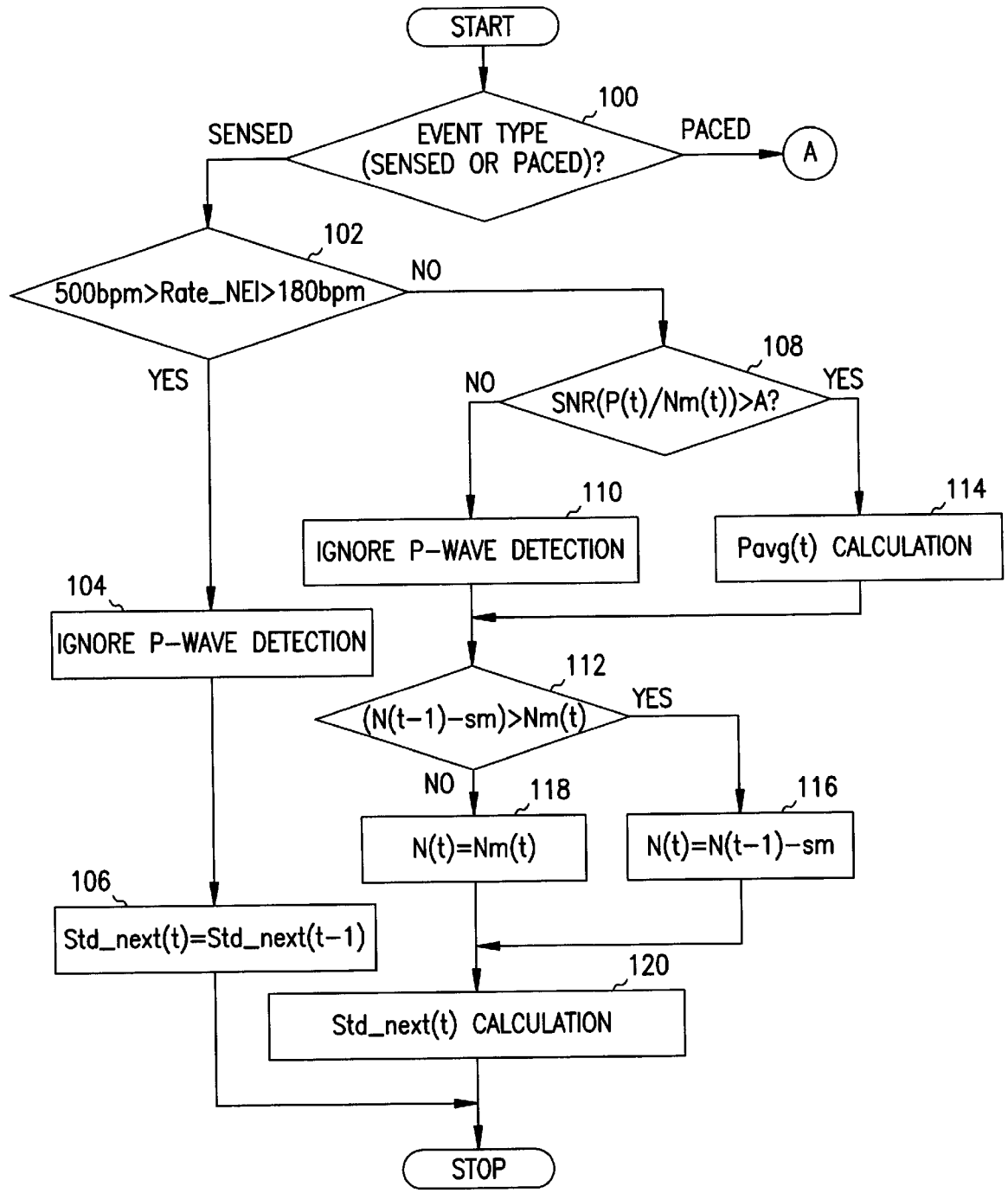
FIGS. 5 and 6 together is a software flow diagram of the autosense algorithm of the present invention following the measurement of noise for atrial autosense.

As described in greater detail below, the software utilized by the controller 28 determines a value for the atrial sensing threshold from the amplitude of the cardiac depolarization, the maximum amplitude of noise during the noise measurement interval, and from the quantity of noise deflections detected during a previous noise measurement interval. The algorithm that may be utilized by the controller 28 during atrial autosense varies depending upon whether an atrial depolarization event or p-wave is detected. Once an atrial depolarization is detected a timer circuit and counter are initialized. At the end of the noise measurement window and PVARP, the controller 28 implements the sequence shown in FIGS. 5 and 6. For ease of discussion, the following definitions apply to the symbols used in the Figures.

| | |
|---|---|
| Rate_NEI | rate of counted deflections during noise measurement interval exceeding the previous sensing threshold |
| Std_next(t) | the next sensing threshold value |
| Std_next(t-1) | the previous sensing threshold value |
| P(t) | the current p-wave amplitude |
| Nm(t) | measured noise amplitude within the current noise measurement interval |
| Pavg(t) | current smoothed p-wave amplitude value |
| Pavg(t-1) | previous smoothed p-wave amplitude value |
| N(t) | current noise level |
| N(t-1) | previous noise level |
| SNR | signal to noise ratio |
| sm | constant |
| RNW | retriggerable noise window |

At the end of the noise measurement interval, the controller 28 implements a subroutine that first determines whether the atrial event during the current cardiac cycle was a detected atrial depolarization event or delivery of an atrial pace or the (see decision block 100). If the atrial event was an atrial pacing stimulus, the controller 28 follows the sequence shown in FIG. 6 which is interconnected with the flowchart in FIG. 5 by connector "A". This path is also followed if no atrial depolarization was detected in the current cardiac cycle due to the occurrence of a premature ventricular contraction or PVC. In the case of either an atrial pace delivered by the device in response to non-detection of a p-wave or the occurrence of a PVC, there is the possibility that a p-wave actually occurred but was undersensed. Furthermore, in the case of a PVC, it has been determined from patient data that the occurrence of a PVC causes subsequent p-waves to be decreased in amplitude. As will be described, the invention therefore provides that the atrial sensing threshold will be adjusted in a manner decreases the threshold. The formula for calculating the atrial sensing threshold in this case results in a decreased atrial sensing threshold unless the current noise level warrants otherwise.

If an intrinsic atrial depolarization was detected, the controller 28 then determines the rate, in deflections per minute (dpm), of the number of deflections during the noise measurement window having an amplitude that exceeds the preceding atrial sensing threshold level (see decision block 102). If the rate of the number of deflections is greater than 180 dpm but less than 500 dpm, the p-wave detection is ignored (see block 104) and the sensing threshold value is set equal to the previous sensing threshold value (see block 106). When the rate of the number of deflections is greater than 180 dpm but less than 500 dpm, it is considered that the detected deflections are the result of atrial flutter or fibrillation. In certain embodiments, the predetermined lower limit may be set equal to the URL, which may preferably be set at 250 dpm.

If the rate of the number of deflections is not between 180–500 dpm, then the signal to noise ratio (SNR) is determined and compared to a predetermined constant A (see decision block 108). The SNR is determined by taking the measured amplitude of the p-wave cardiac depolarization and dividing by the measured noise amplitude, wherein the measured noise amplitude may be either the maximum amplitude of noise detected during the noise measurement interval or the average of all noise deflections detected during the noise measurement interval. The predetermined constant A is preferably set at 2 but may range between 1.5–5. If the SNR does not exceed the preset constant A, the p-wave detection is ignored, (see block 110) and the controller determines whether the previous noise level minus a constant "sm" exceeds the measured noise level (see decision block 112). If the SNR exceeds the preset constant A, then the current "smoothed" or average p-wave amplitude (Pavg(t)) is determined (see block 114) in accordance with the following formula:

$$Pavg(t)=P(t)/4+((3)Pavg(t-1))/4$$

where P(t) is the current measured p-wave amplitude and Pavg(t−1) is the value for the smoothed or average p-wave amplitude for the previous cardiac cycle. Once the Pavg(t) is determined, then the controller determines whether the previous noise level minus a constant "sm" exceeds the measured noise level (see decision block 112), where constant sm, without limitation, may range between 0.01–0.5 mV, with 0.05 mV being preferred. If the previous noise level minus constant sm exceeds the current measured noise amplitude, the noise level is set equal to the previous noise level minus the constant sm (see block 116), otherwise, the noise level is set equal to the measured noise amplitude within the current noise measurement interval (see block 118). Once a noise level value and "smoothed" p-wave value have been determined, the next atrial sensing threshold is determined in accordance with the following:

$$Stdnext(t)=Max[(Pavg(t)-N(t))/x+N(t); ymV; zN(t)]$$

where x, y, and z are constant values having a range as previously described. The controller 28 then sets the ATH 32, for example, equal to the calculated value and atrial sensing continues with that threshold until autosensing is performed again during the next cardiac cycle.

Figure 6:
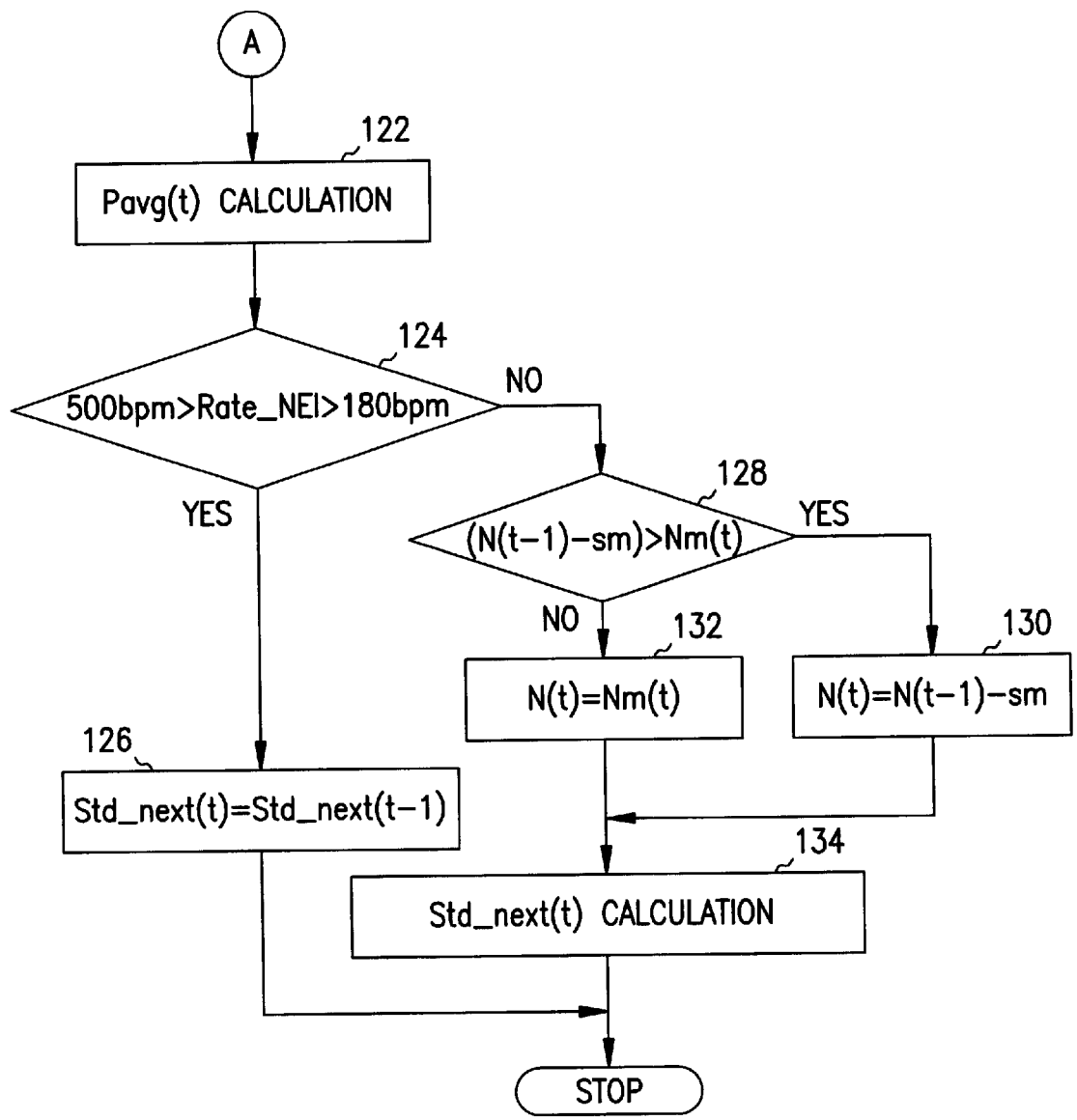

Referring again to connector "A" and FIG. 6, if no atrial depolariztion was detected so that the cardiac event was either delivery of an atrial pacing stimulus or the occurrence of a premature ventricular contraction, following the end of the noise measurement interval the controller 28 determines the "smoothed" or average p-wave amplitude (see block 122) from the following equation:

$$Pavg(t)=Pavg(t-1)-sm$$

In an alternative embodiment, the average p-wave amplitude is calculated as:

$$Pavg(t)=Pavg(t-1)(Y)$$

where Y is a specified constant less than 1.0. Once a value for the "smoothed" or average p-wave amplitude is determined, the controller 28 then determines the rate, in deflections per minute (dpm), of the number of deflections during the noise measurement window having an amplitude that exceeds the preceding atrial sensing threshold level (see decision block 124). If the rate of the number of deflections is greater than 180 dpm but less than 500 dpm, the next atrial sensing threshold is set equal to the previous atrial sensing threshold value (see block 126).

If the rate of the number of deflections is not between 180–500 dpm, then the controller determines whether the previous noise level minus a constant "sm" exceeds the measured noise level (see decision block 128), where constant sm, without limitation, may range between 0.01–0.05 mV, with 0.05 mV being preferred. If the previous noise level minus constant sm exceeds the current measured noise amplitude, the noise level is set equal to the previous noise level minus the constant sm (see block 130), otherwise, the noise level is set equal to the measured noise amplitude within the current noise measurement window (see block 132). Once a current noise level and average p-wave amplitude have been determined, the next atrial sensing threshold is determined in accordance with the following:

$$Stdnext(t)=Max[(Pavg(t)-N(t))/x+N(t); ymV; zN(t)]$$

where x, y, and z are constant values having a range as previously described. The controller 28 then sets the ATH 32, for example, equal to the calculated atrial sensing threshold value.

Figure 7:
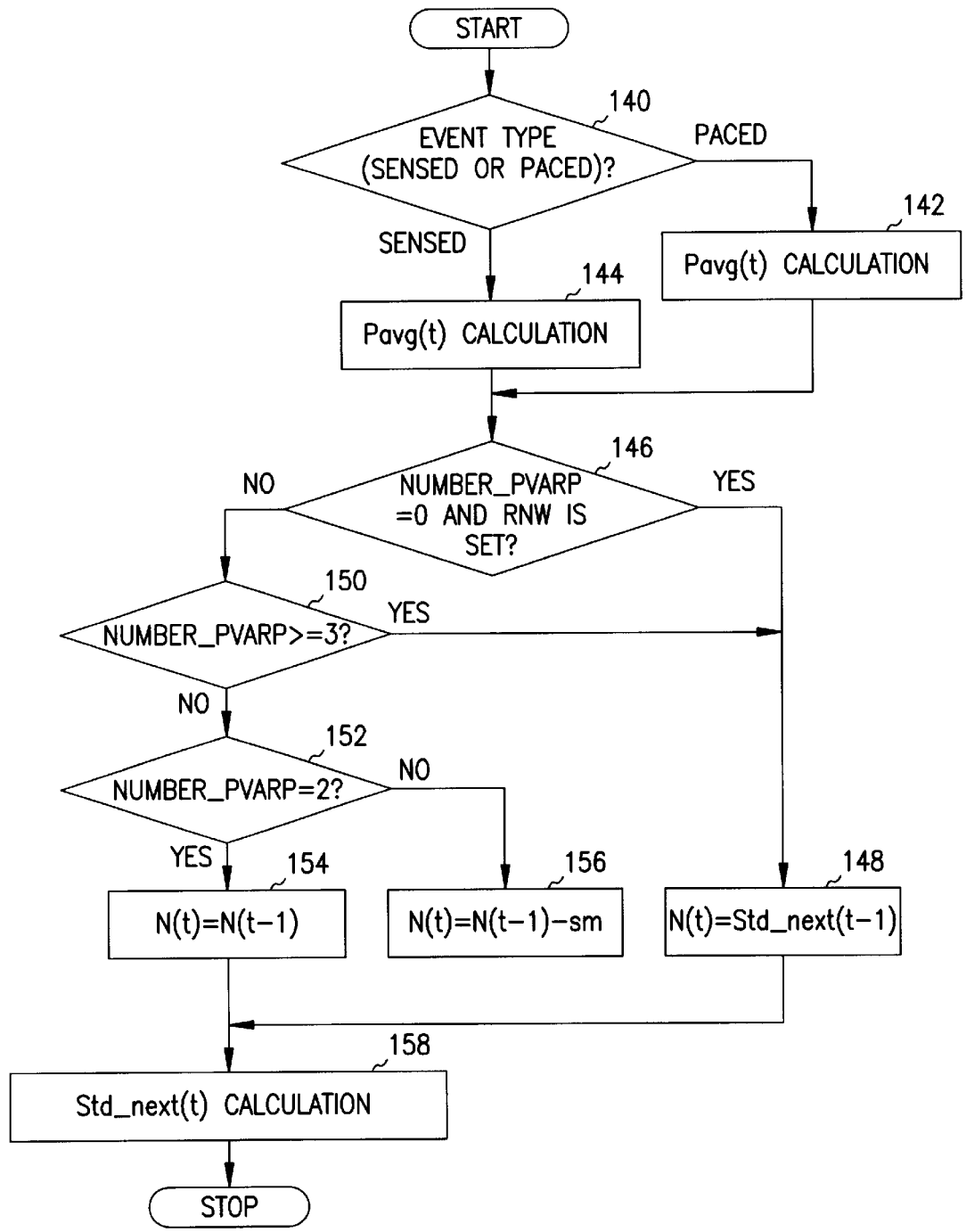
FIG. 7 is a software flow diagram of an alternate autosense algorithm of the present invention for atrial autosense.
Figure 8:
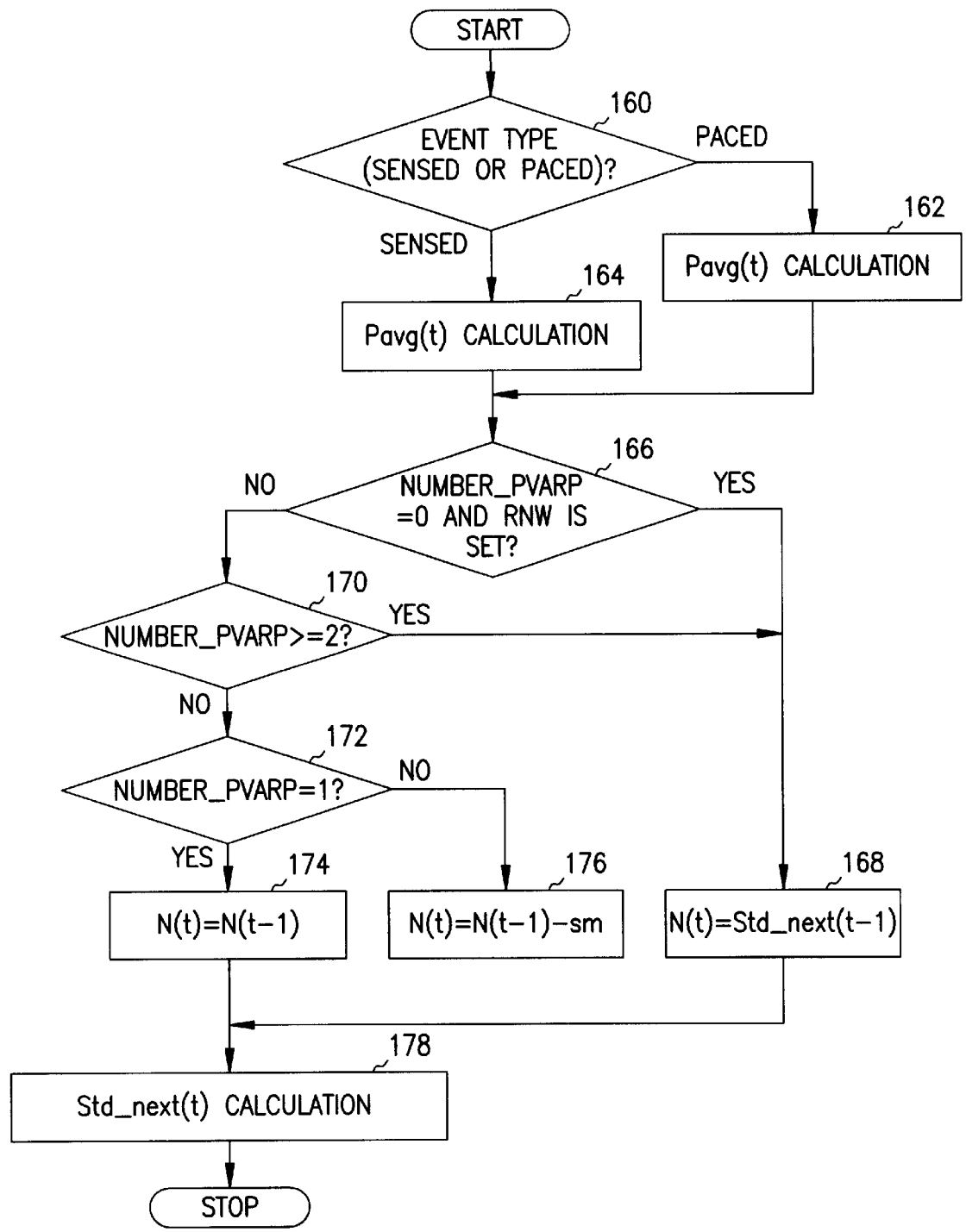
FIG. 8 is a software flow diagram of an alternate autosense algorithm of the present invention for atrial autosense.

Referring next to FIGS. 7 and 8, alternate preferred algorithms are shown that may be implemented by a cardiac rhythm management device incapable of a direct measurement of the amplitude of noise while in an atrial autosense mode. The sequence shown in FIG. 7 is implemented by the controller 28 when the PVARP is set equal to 250 ms or the PVARP exceeds 250 ms. The sequence shown in FIG. 8 is implemented when the PVARP is less than 250 ms. In the case where PVARP exceeds 250 ms, the "smoothed" p-wave amplitude and the number of events exceeding the sensing threshold is determined over a preset period (250 ms) of time or noise measurement interval within the PVARP interval.

The sequence shown in FIG. 7 is implemented by the controller after the noise measurement interval or PVARP times out. The controller 28 then determines whether the current atrial event is a pace or detected atrial depolarization (see decision block 140). If no p-wave is detected, so that the event is either an atrial pace or occurrence of a premature ventricular contraction, the controller 28 calculates the current average p-wave amplitude (see block 142) in accordance with the following equation:

$$Pavg(t)=Pavg(t-1)-sm$$

where, without limitation, sm is a constant ranging between 0.01–0.5 mV, with 0.05 mV being preferred. If an atrial depolarization event was detected, the controller 28 calculates the "smoothed" or average amplitude (see block 144) for the detected p-wave deflection in accordance with the following equation as previously described:

$$Pavg(t)=P(t)/4+((3)Pavg(t-1))/4$$

The controller then determines the number of deflections counted exceeding the sensing threshold during the predetermined period. If there were no deflections detected during the noise measurement interval and the retriggerable noise window of 40 ms, for example. is set (see decision block 146), then the noise level is set equal to the previous sensing threshold value (see block 148). If deflections are detected during the noise measurement interval, and the number of detected deflections exceed 3 (see decision block 150), then the noise level is set equal to the previous atrial sensing threshold value (see block 148). If the number of detected deflections equals 2 (see decision block 152), then the noise level is set equal to the previous noise level (see decision block 154), otherwise the noise level is set equal to the previous noise level minus a constant "sm" as previously described (see block 156). In this manner the noise level is estimated for the current noise measurement interval. Once the "smoothed" or average p-wave amplitude and the noise level are calculated, then the value for the next atrial sensing threshold is determined in accordance with the following:

$$\text{Stdnext}(t)=\text{Max}[(Pavg(t)-N(t))/x+N(t); ymV; zN(t)]$$

where x, y, and z are constant values having a range as previously described. The controller 28 then sets the ATH register 32, for example, equal to the calculated value and sensing continues until the next cardiac depolarization is sensed.

As previously indicated, the sequence shown in FIG. 8 is implemented by the controller 28 after the noise measurement window or predetermined period times out and when the PVARP is less than 250 ms. When this is the case, the controller 28 determines whether the current atrial event is a detected atrial depolarization or delivery of an atrial pace (see decision block 160). If no p-wave was detected so that either an atrial pace stimulus was delivered or a premature ventricular contraction occurred, the controller 28 calculates the "smoothed" or average p-wave amplitude (see block 162) in accordance with the following equation:

$$Pavg(t)=Pavg(t-1)-dm$$

where, without limitation sm is a constant ranging between 0.01–0.5 mV with 0.05 mV being preferred. If an atrial depolarization event was detected, the controller 28 calculates the "smoothed" or average p-wave amplitude (see block 164) in accordance with the following equation as previously described:

$$Pavg(t)=P(t)/4+((3)Pavg(t-1))/4$$

The controller then determines the number of deflections counted exceeding the atrial sensing threshold during the PVARP interval. If there were no deflections detected during the noise measurement window, and the retriggerable noise window of 40 ms for example, is set (see decision block 166), then the noise level is set equal to the previous atrial sensing threshold value (see block 168). If deflections are detected during the noise measurement window, and the number of detected deflections exceed 2 (see decision block 170), then the noise level is set equal to the previous sensing threshold value (see block 168). If the number of detected deflections equals 1 (see decision block 172), then the noise level is set equal to the previous noise level (see decision block 174), otherwise, the noise level is set equal to the previous noise level minus a constant "sm" as previously described (see block 176). In this manner the noise level is estimated for the current noise measurement interval. Once the current "smoothed" or average p-wave amplitude and noise level are calculated, then the value for the next atrial sensing threshold is determined in accordance with the following:

$$\text{Stdnext}(t)=\text{Max}[(Pavg(t)-N(t))/x+N(t); ymV; zN(t)]$$

where x, y, and z are constant values having a range as previously described. The controller 28 then sets the ATH register 32, for example, equal to the calculated value and sensing continues.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for automatically adjusting a sensing threshold in a cardiac rhythm management device, comprising:

sensing a ventricular electrogram signal with a ventricular sensing channel and detecting a ventricular depolarization event when the sensed ventricular signal exceeds a ventricular sensing threshold;

sensing an atrial electrogram signal with an atrial sensing channel and detecting an atrial depolarization event when the sensed atrial signal exceeds an atrial sensing threshold;

adjusting the sensing threshold for a sensing channel for a current cardiac cycle during a refractory period beginning with either detection of an r-wave or delivery of a ventricular pacing pulse by the device, wherein the sensing threshold is based upon a measured amplitude of a depolarization event detected through the sensing channel and a noise level measured during a post-ventricular refractory period of the current cardiac cycle; and, wherein the adjustment of the sensing threshold for a sensing channel is performed in a manner that results in a decrease of the sensing threshold for that channel if no depolarization event was detected during the current cardiac cycle in that channel and a noise level for the channel is unchanged from the previous cardiac cycle.

2. The method of claim 1 wherein the adjustment results in a decrease of the atrial sensing threshold if no p-wave is detected during the current cardiac cycle with no atrial pace being delivered unless the adjusted atrial sensing threshold would then be below a minimum value.

3. The method of claim 1 wherein, if no p-wave is detected during the current cardiac cycle, the atrial sensing threshold is decreased by a first specified amount if an atrial pacing pulse is delivered at the beginning of the current cardiac cycle, and decreased by a second specified amount if an r-wave is detected during the current cardiac cycle with no preceding p-wave so as to represent either a premature ventricular contraction or an atrial undersense.

4. The method of claim 1 further comprising:

measuring the amplitude of p-waves;

decreasing the atrial sensing threshold within a noise measurement window that occurs during a refractory period;

measuring the amplitudes of atrial electrogram signals that exceed the atrial sensing threshold during the noise measurement window and computing a current atrial noise level N(t) based upon the measured amplitudes; and, adjusting the atrial sensing threshold based upon the measured amplitude of a detected p-wave and the current noise level.

5. The method of claim 4 wherein the atrial sensing threshold is adjusted by the following formula if no p-wave is detected in the current cardiac cycle and an r-wave is detected:

$$ST(t)=N(t)+[ST(t-1)-N(t)]/Z$$

where ST(t) and ST(t-1) are current and previous atrial sensing thresholds, respectively, and N(t) is the current atrial noise level, and Z is a constant between 1 and 6.

6. The method of claim 4 wherein the atrial sensing threshold is adjusted based upon the current noise level and a current average p-wave amplitude Pavg(t) computed from a combination of a previous average p-wave amplitude computed for a previous cardiac cycle and, if a p-wave is detected in the current cardiac cycle, the current p-wave amplitude according to the following formula:

$$Pavg(t)=(A)P(t)+(B)Pavg(t-1)$$

where A and B are constants, P(t) is the p-wave amplitude measured in the current cardiac cycle, and Pavg(t-1) is a previous average p-wave amplitude computed for a previous cardiac cycle.

7. The method of claim 6 wherein the current average p-wave amplitude Pavg(t) is computed calculated according to the following formula if no p-wave is detected and either an atrial pacing pulse was delivered or an r-wave was detected during the current cardiac cycle:

$$Pavg(t)=Pavg(t-1)-sm$$

where sm is a specified constant.

8. The method of claim 7 wherein the constant sm corresponds to a multiple of the minimum resolution of an analog-to-digital converter used to process an electrogram signal.

9. The method of claim 7 wherein separate values of sm are used in computing Pavg(t) depending upon whether the non-detection of a p-wave during the current cardiac cycle is due to an atrial pacing pulse being delivered or to the occurrence of an r-wave with no preceding p-wave.

10. The method of claim 1 further comprising:

measuring the amplitude of r-waves;

decreasing the ventricular sensing threshold within a noise measurement window that occurs during a ventricular refractory period;

measuring the amplitudes of ventricular electrogram signals that exceed the decreased sensing threshold during the noise measurement window and computing a current ventricular noise level VN(t) based upon the measured amplitudes; and, adjusting the ventricular sensing threshold based upon the measured amplitude of a detected r-wave and the current ventricular noise level.

11. A cardiac rhythm management device, comprising:

atrial and ventricular sensing channels for sensing atrial and ventricular electrogram signals, each channel including an electrode and a sense amplifier;

an atrial threshold detector for detecting p-waves when the sensed atrial electrogram signal exceeds an atrial sensing threshold;

a ventricular threshold detector for detecting r-waves when the sensed ventricular electrogram signal exceeds a ventricular sensing threshold;

a pulse generator and associated control circuitry for delivering pacing pulses to the atrium and/or ventricle in response to elapsed time intervals and detected r-waves and p-waves;

circuitry for adjusting the sensing threshold for a sensing channel for a current cardiac cycle during a refractory period beginning with either detection of an r-wave or delivery of a ventricular pacing pulse by the device, wherein the sensing threshold is based upon a measured amplitude of a depolarization event detected through the sensing channel and a noise level measured during a post-ventricular refractory period of the current cardiac cycle; and, wherein the adjustment of the sensing threshold for a sensing channel is performed in a manner that results in a decrease of the sensing threshold for that channel if no depolarization event was detected during the current cardiac cycle in that channel and a noise level for the channel is unchanged from the previous cardiac cycle.

12. The device of claim 11 wherein the adjustment results in a decrease of the atrial sensing threshold if no p-wave is detected during the current cardiac cycle with no atrial pace being delivered unless the adjusted atrial sensing threshold would then be below a minimum value.

13. The device of claim 11 wherein the sensing threshold adjustment circuitry operates such that, if no p-wave is detected during the current cardiac cycle, the atrial sensing threshold is decreased by a first specified amount if an atrial pacing pulse is delivered at the beginning of the current cardiac cycle, and decreased by a second specified amount if an r-wave is detected during the current cardiac cycle with no preceding p-wave so as to represent either a premature ventricular contraction or an atrial undersense.

14. The device of claim 11 further comprising circuitry for:

measuring the amplitude of p-waves;

decreasing the atrial sensing threshold within a noise measurement window that occurs during a refractory period;

measuring the amplitudes of atrial electrogram signals that exceed the atrial sensing threshold during the noise measurement window and computing a current atrial noise level N(t) based upon the measured amplitudes; and, adjusting the atrial sensing threshold based upon the measured amplitude of a detected p-wave and the current noise level.

15. The device of claim 14 wherein the threshold adjusting circuitry adjusts the atrial sensing by the following formula if no p-wave is detected in the current cardiac cycle and an r-wave is detected:

$$ST(t)=N(t)+[ST(t-1)-N(t)]/Z$$

where $ST(t)$ and $ST(t-1)$ are current and previous atrial sensing thresholds, respectively, and $N(t)$ is the current atrial noise level, and Z is a constant between 1 and 6.

16. The device of claim 14 wherein the threshold adjusting circuitry adjusts the atrial sensing threshold based upon the current noise level and a current average p-wave amplitude $Pavg(t)$ computed from a combination of a previous average p-wave amplitude computed for a previous cardiac cycle and, if a p-wave is detected in the current cardiac cycle, the current p-wave amplitude according to the following formula:

$$Pavg(t)=(A)P(t)+(B)Pavg(t-1)$$

where A and B are constants, $P(t)$ is the p-wave amplitude measured in the current cardiac cycle, and $Pavg(t-1)$ is a previous average p-wave amplitude computed for a previous cardiac cycle.

17. The device of claim 16 wherein the current average p-wave amplitude $Pavg(t)$ is computed calculated according to the following formula if no p-wave is detected and either an atrial pacing pulse was delivered or an r-wave was detected during the current cardiac cycle:

$$Pavg(t)=Pavg(t-1)-sm$$

where sm is a specified constant.

18. The device of claim 17 wherein the constant sm corresponds to a multiple of the minimum resolution of an analog-to-digital converter used to process an electrogram signal.

19. The device of claim 17 wherein separate values of sm are used in computing $Pavg(t)$ depending upon whether the non-detection of a p-wave during the current cardiac cycle is due to an atrial pacing pulse being delivered or to the occurrence of an r-wave with no preceding p-wave.

20. The device of claim 11 further comprising circuitry for:

measuring the amplitude of r-waves;

decreasing the ventricular sensing threshold within a noise measurement window that occurs during a ventricular refractory period;

measuring the amplitudes of ventricular electrogram signals that exceed the decreased sensing threshold during the noise measurement window and computing a current ventricular noise level $VN(t)$ based upon the measured amplitudes; and, adjusting the ventricular sensing threshold based upon the measured amplitude of a detected r-wave and the current ventricular noise level.

* * * * *